(12) United States Patent
Glazer et al.

(10) Patent No.: US 11,026,808 B2
(45) Date of Patent: Jun. 8, 2021

(54) BONE GRAFTING AND COMPACTION

(71) Applicant: Glazer Paul Andrew, Boston, MA (US)

(72) Inventors: Paul Andrew Glazer, Boston, MA (US); Andrew Ziegler, Arlington, MA (US)

(73) Assignee: Alphatec Spine, Inc., Carlsbad, CA (US)

( * ) Notice: Subject to any disclaimer, the term of this patent is extended or adjusted under 35 U.S.C. 154(b) by 22 days.

(21) Appl. No.: 16/163,102

(22) Filed: Oct. 17, 2018

(65) Prior Publication Data
US 2019/0110903 A1    Apr. 18, 2019

Related U.S. Application Data

(60) Provisional application No. 62/573,856, filed on Oct. 18, 2017.

(51) Int. Cl.
*A61F 2/46* (2006.01)
*A61B 17/34* (2006.01)
(Continued)

(52) U.S. Cl.
CPC ........ *A61F 2/4601* (2013.01); *A61B 17/3421* (2013.01); *A61F 2/4455* (2013.01);
(Continued)

(58) Field of Classification Search
CPC ............ A61F 2/4601; A61F 2002/4625; A61F 2002/4627; A61F 2/4644; A61F 2/46;
(Continued)

(56) References Cited

U.S. PATENT DOCUMENTS 5,265,956 A * 11/1993 Nelson ............... A61B 17/8822
141/23
5,431,654 A * 7/1995 Nic .................... A61B 17/8822
606/92

(Continued)

FOREIGN PATENT DOCUMENTS

GB      2348252 A  *  9/2000  .............. F04B 13/02
GB      2550583 A  * 11/2017  ............ B01F 15/027

*Primary Examiner* — Matthew J Lawson
*Assistant Examiner* — Lisa Nguyen
(74) *Attorney, Agent, or Firm* — Joshua L. Jones; Gabrielle L. Gelozin

(57) ABSTRACT

A tool for delivery and/or compaction of bone graft material includes a cannula with an inner lumen extending along a longitudinal axis from a hopper end of the cannula to a delivery tip of the cannula. A hopper with an internal volume for storing bone graft material is connected to the hopper end of the cannula with the internal volume of the hopper in communication with the inner lumen of the cannula for delivery of bone graft material from the hopper to the delivery tip of the cannula. An output shaft within the inner lumen extends along the longitudinal axis. The output shaft includes a helical screw thread extending radially outward from the output shaft toward an inner surface of the cannula. An actuator is connected to the hopper and to the output shaft to drive the output shaft rotationally relative to the hopper and to the cannula.

14 Claims, 9 Drawing Sheets

(51) Int. Cl.
| | | |
|---|---|---|
| *A61F 2/44* | (2006.01) | |
| *A61B 17/88* | (2006.01) | |
| *A61F 2/28* | (2006.01) | |
| *A61B 17/00* | (2006.01) | |
| *A61F 2/30* | (2006.01) | |
| *A61F 2/36* | (2006.01) | |

(52) U.S. Cl.
CPC ....... *A61B 17/3472* (2013.01); *A61B 17/8802* (2013.01); *A61B 17/885* (2013.01); *A61B 2017/00685* (2013.01); *A61F 2/36* (2013.01); *A61F 2002/2835* (2013.01); *A61F 2002/3069* (2013.01); *A61F 2002/30471* (2013.01); *A61F 2002/30579* (2013.01)

(58) Field of Classification Search
CPC ......... A61F 2002/2835; A61B 17/8822; A61B 17/8805; A61B 2017/8838
See application file for complete search history.

(56) References Cited

U.S. PATENT DOCUMENTS

| | | | | |
|---|---|---|---|---|
| 5,876,116 A | * | 3/1999 | Barker | A61B 17/8825 222/241 |
| 6,024,480 A | * | 2/2000 | Seaton | B01F 7/24 206/222 |
| 7,854,543 B2 | * | 12/2010 | Coffeen | B01F 7/00116 366/189 |
| 2018/0132918 A1 | * | 5/2018 | Insley | A61B 17/7098 |

* cited by examiner

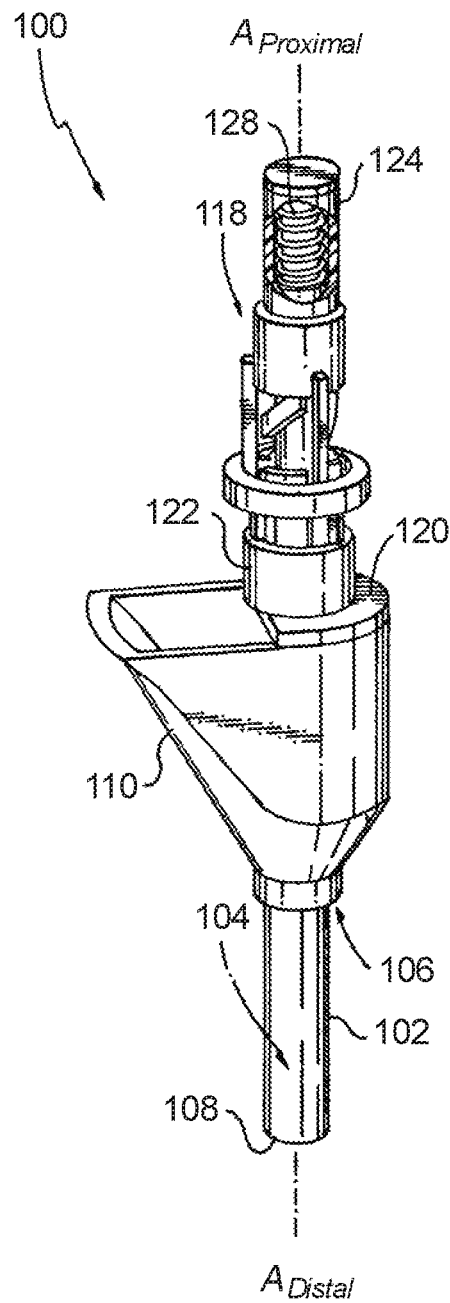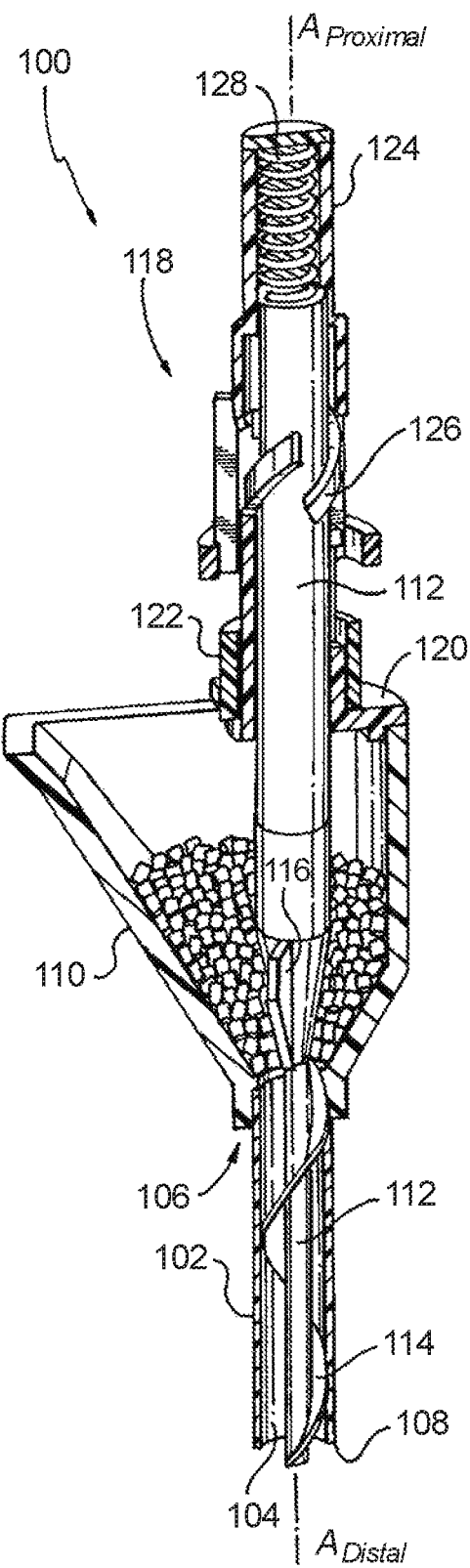
Fig. 1
Fig. 2

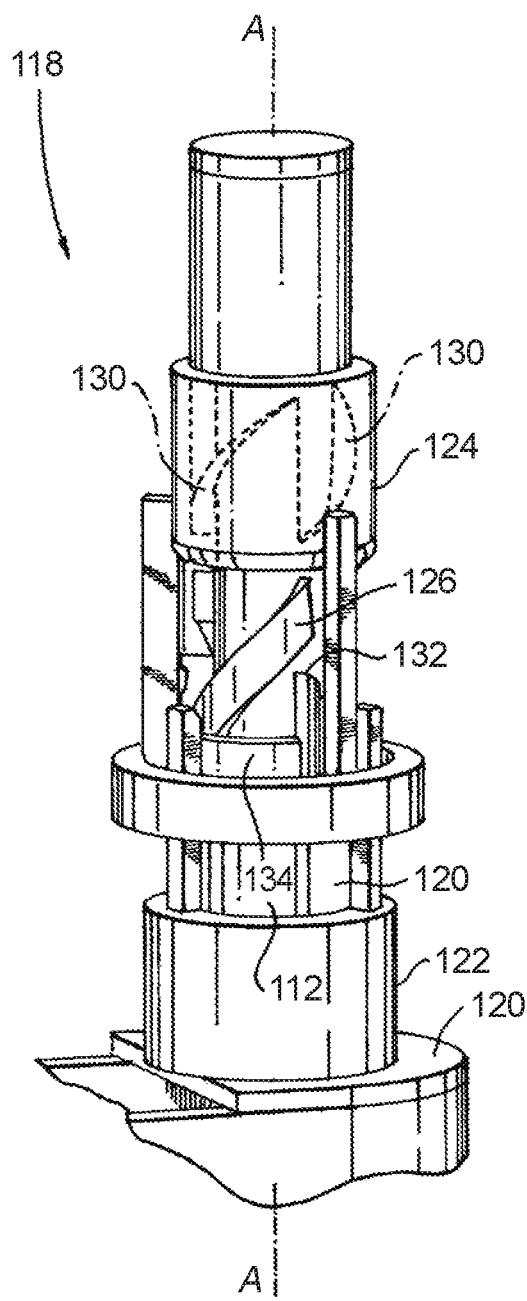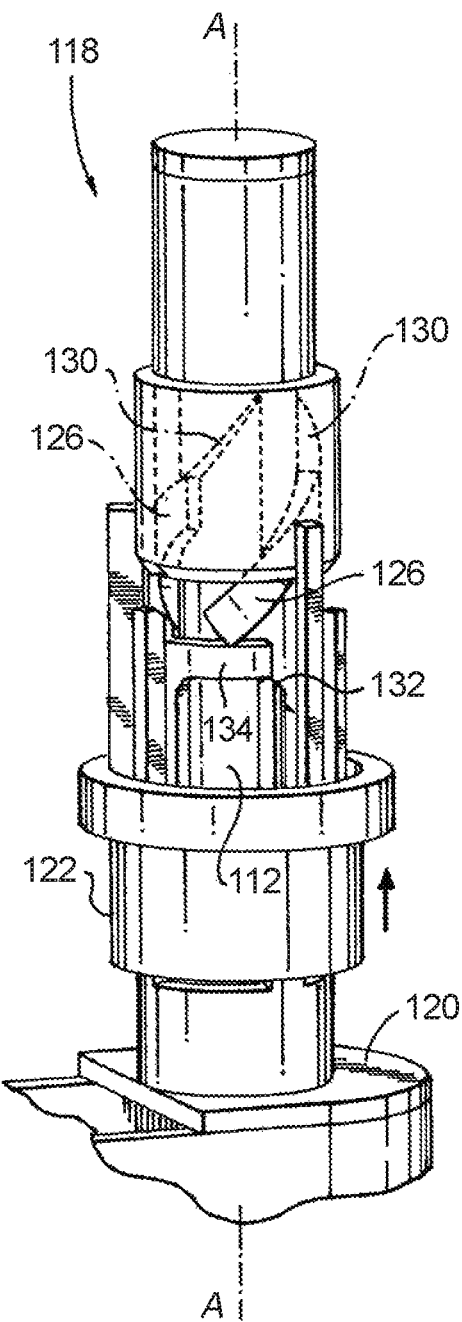
Fig. 4
Fig. 5

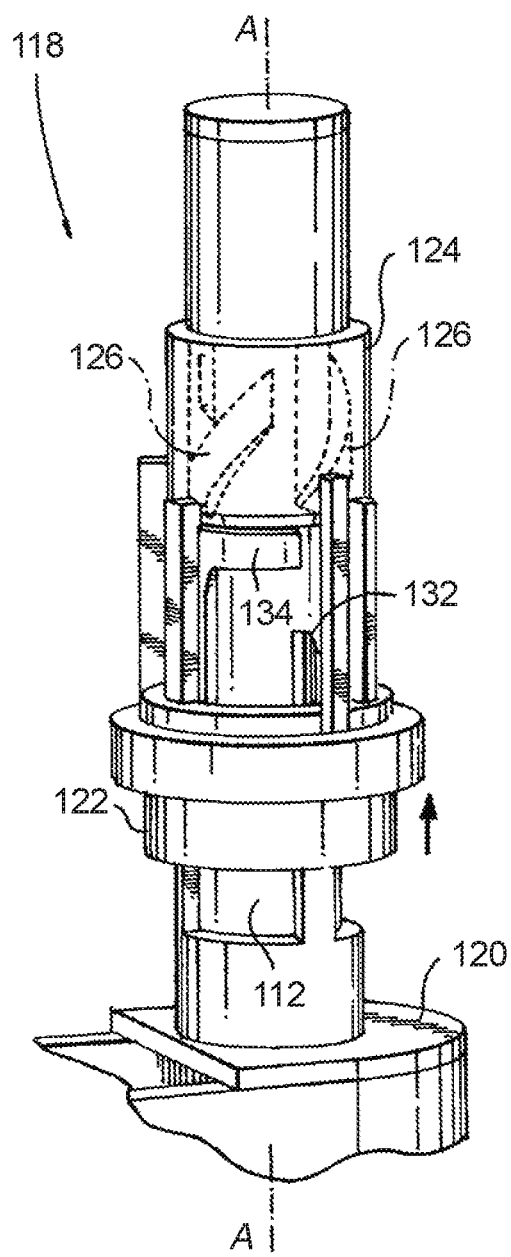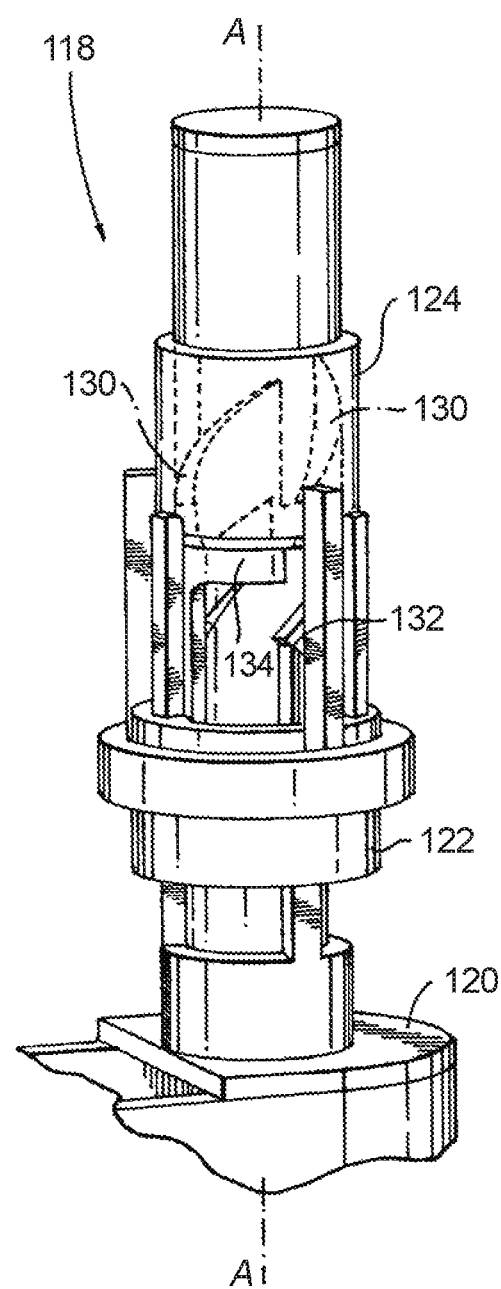
Fig. 6
Fig. 7

BONE GRAFTING AND COMPACTION

CROSS-REFERENCE TO RELATED APPLICATIONS

This application claims benefit of priority to U.S. Provisional Patent Application No. 62/573,856 filed Oct. 18, 2017, which is incorporated by reference herein in its entirety.

BACKGROUND OF THE INVENTION

1. Field of the Invention

The present disclosure relates to bone grafting and compaction, and more particularly to tools and methods for bone grafting and compaction.

2. Description of Related Art

There are many orthopedic applications where bone grafting is necessary. Bone grafts generally fall into different categories based on the source of the bone graft material. An autograft utilizes bone from a patient's own body and is often harvested from the patient's iliac crest. An allograft utilizes bone tissue from someone other than the patient, and can be harvested from a cadaver. Often allograft material is provided as small pellets that are planted in a patent where bone growth is needed. In addition to autograft and allograft, there are synthetic variants.

During a surgical operation that involves bone grafting, the bone graft material must be delivered to the site where bone growth is needed. Once in place, the bone graft material typically needs to be compacted to ensure proper integration. The delivery and compaction of bone graft material can be complicated where the bone graft site is small and/or the procedure is minimally invasive. For example, delivery and compaction of bone graft material for procedures on spinal arch pedicles can be difficult using traditional techniques.

The conventional techniques have been considered satisfactory for their intended purpose. However, there is an ever present need for improved delivery and compaction of bone graft material. This disclosure provides a solution for this need.

SUMMARY OF THE INVENTION

A tool for delivery and/or compaction of bone graft material includes a cannula with an inner lumen extending along a longitudinal axis from a hopper end of the cannula to a delivery tip of the cannula. A hopper with an internal volume for storing bone graft material is connected to the hopper end of the cannula with the internal volume of the hopper in communication with the inner lumen of the cannula for delivery of bone graft material from the hopper to the delivery tip of the cannula. An output shaft within the inner lumen extends along the longitudinal axis. The output shaft includes a helical screw thread extending radially outward from the output shaft toward an inner surface of the cannula. An actuator is connected to the hopper and to the output shaft to drive the output shaft rotationally relative to the hopper and to the cannula.

The actuator can be configured to withdraw the output shaft axially along the longitudinal axis in a direction into the hopper while rotating the output shaft for engaging bone graft material with the helical screw thread in the hopper. The actuator can be configured to extend the output shaft axially along the longitudinal axis in a direction out of the hopper for pushing bone graft material engaged with the helical screw thread out of the hopper and out of the inner lumen of the cannula. The actuator can be configured to extend the output shaft axially along the longitudinal axis in a direction out of the hopper without rotating the output shaft for at least part of a stroke. The actuator can be configured to convert reciprocating linear input movement into motion of the output shaft that alternates between linear motion extending along the longitudinal axis to push bone graft material out of the inner lumen of the cannula and combined linear and rotary motion withdrawing in a direction toward the internal volume of the hopper so that continued reciprocating linear input movement repeatedly moves bone graft material from the hopper to the delivery tip of the cannula.

A paddle can extend radially outward from the output shaft within the internal volume of the hopper for agitating bone graft material within the hopper upon rotation of the output shaft. The paddle can be proximal of the helical screw thread.

The actuator can include a bottom cam mounted stationary relative to the hopper. A driver can be engaged for sliding linear motion relative to the bottom cam. A top cam can be mounted stationary relative to the hopper. The output shaft can include at least one cam follower configured to alternately cam with the bottom cam and with the top cam to convert reciprocating linear input movement of the driver into motion of the output shaft that alternates between linear motion extending along the longitudinal axis to push bone graft material out of the inner lumen of the cannula and combined linear and rotary motion withdrawing in a direction toward the internal volume of the hopper so that continued reciprocating linear input movement of the driver repeatedly moves bone graft material from the hopper to the delivery tip of the cannula.

A biasing member can be mounted to bias the output shaft in a direction toward the delivery tip of the cannula, wherein biasing force of the biasing member must be overcome to move the driver and output shaft in a direction away from the delivery tip of the cannula. The top cam can include at least one camming surface configured to rotate the output shaft as the driver presses the at least one cam follower of the drive shaft into the at least one camming surface of the top cam. The bottom cam can include at least one camming surface configured to rotate the output shaft as the output shaft is biased toward the delivery tip of the cannula to rotationally position the output shaft for a subsequent camming against the top cam.

A method of delivering bone graft material to a bone graft site includes withdrawing a portion of an output shaft into a hopper housing bone graft material to engage the bone graft material in the hopper. The method also includes pushing the portion of the output shaft axially out of the hopper to deliver bone graft material from the hopper to a bone graft site.

The output shaft can include a helical screw thread, and withdrawing the portion of the output shaft into the hopper can include withdrawing the helical screw thread helically by combined linear and rotary motion. Helically withdrawing can include driving the output shaft with helical motion that follows the helical screw thread to keep in place bone graft material in a cannula housing at least a portion of the helical screw thread. The cannula can be connected at one end to a hopper and can include a delivery tip at an end opposite the hopper, wherein delivering bone graft material from the hopper to a bone graft site includes ejecting bone graft material from the delivery tip of the cannula to a bone graft site. The method can include compacting bone graft material into the bone graft site using applied pressure from at least one of the cannula, the helical screw thread, and/or the output shaft.

Withdrawing the portion of the output shaft, pushing the portion of the output shaft, delivering bone graft material, and compacting bone graft material into the bone graft site can be repeated. Repeatedly withdrawing the portion of the output shaft, pushing the portion of the output shaft, delivering bone graft, and compacting bone graft material into the bone graft site can be driven by reciprocating linear motion of an actuator operatively connected to the output shaft.

The method can include agitating the bone graft material within the hopper using rotary motion of at least one paddle extending radially from the output shaft. The method can include compacting bone graft material from the hopper into at least two different bone graft sites with a single bone graft delivery tool comprising the hopper and the output shaft.

The method can include expanding an intervertebral body in situ, wherein delivering bone graft material from the hopper to a bone graft site includes delivering bone graft material to an interior space of the intervertebral body after expanding the intervertebral body in situ. It is also contemplated that delivering bone graft material from the hopper to a bone graft site includes delivering bone graft material to a proximal femur during a hip revision procedure, or to any other suitable site during any other suitable procedure.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 1 is a perspective view of an exemplary embodiment of a tool for delivery and/or compaction of bone graft material constructed in accordance with the present disclosure, showing the actuator connected to the hopper and the output shaft in the cannula;

FIG. 2 is a partially cross-sectional perspective view of the tool of FIG. 1, showing the output shaft;

FIG. 4 is schematic a perspective view of the actuator of FIG. 3, showing a first stage in actuating the tool, wherein the top cam is shown as though transparent to reveal underlying structures;

FIG. 5 is a schematic perspective view of the actuator of FIG. 4, showing the driver moving axially upward to drive the cam followers of the output shaft into the camming surfaces of the top cam;

FIG. 6 is a schematic perspective view of the actuator of FIG. 4, showing the end of the upward motion of the driver;

FIG. 7 is a schematic perspective view of the actuator of FIG. 4, showing downward movement of the output shaft;

DETAILED DESCRIPTION OF THE PREFERRED EMBODIMENTS

Figure 3:
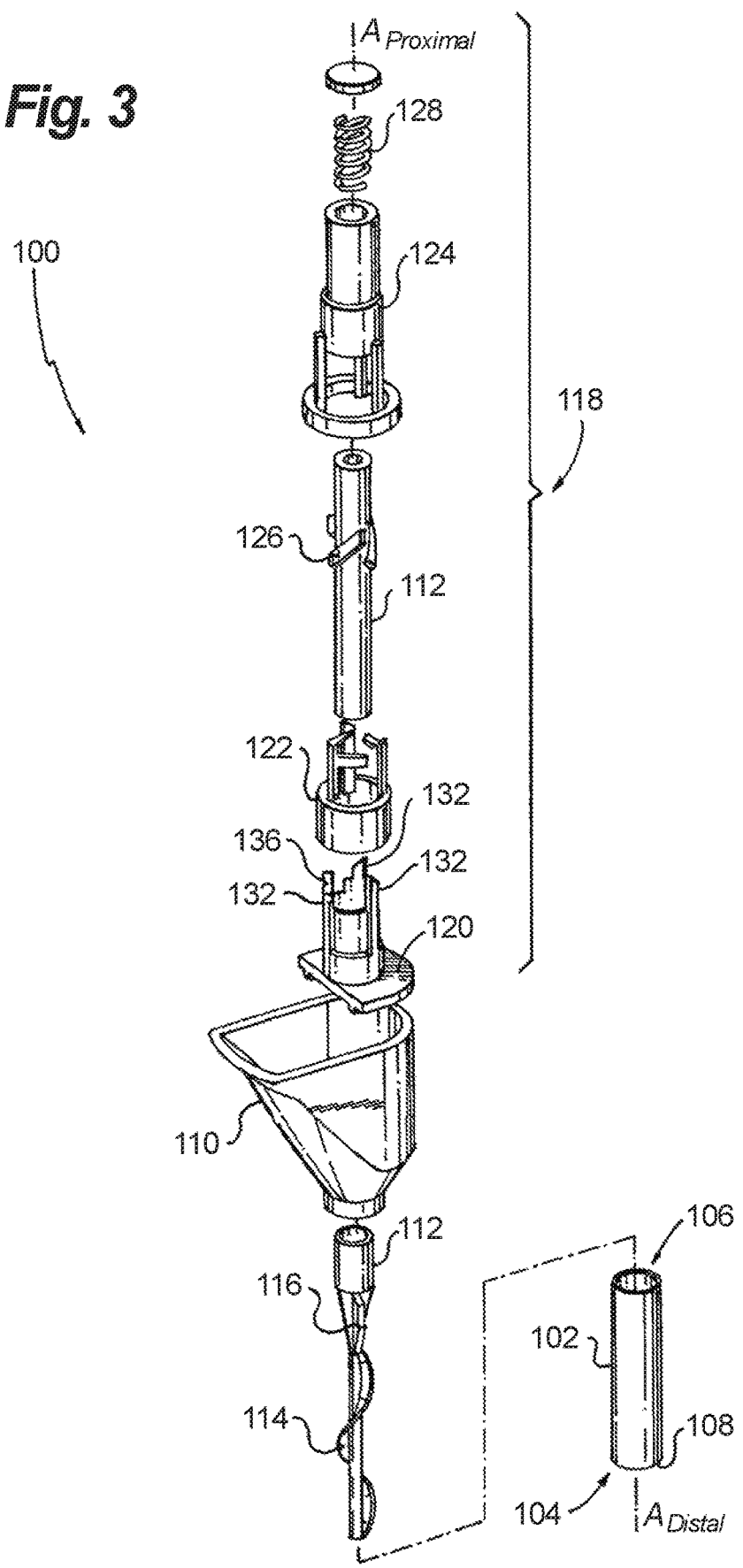
FIG. 3 is a an exploded perspective view of the tool of FIG. 1, showing the top cam, bottom cam, and driver of the actuator separated from one another.

Reference will now be made to the drawings wherein like reference numerals identify similar structural features or aspects of the subject disclosure. For purposes of explanation and illustration, and not limitation, a partial view of an exemplary embodiment of a tool for delivery and/or compaction of bone graft material in accordance with the disclosure is shown in FIGS. 1-2 and is designated generally by reference character 100. Other embodiments of tools in accordance with the disclosure, or aspects thereof, are provided in FIGS. 3-17, as will be described. The systems and methods described herein can be used to deliver and compact bone graft material in bone graft sites for orthopedic procedures, e.g., to improve bone screw fixation such as in pedicle screw fixation for spinal procedures.

A tool 100 for delivery and compaction of bone graft material includes a cannula 102 with an inner lumen 104 extending along a longitudinal axis A from a hopper end 106 of the cannula 102 to a delivery tip 108 of the cannula 102. Longitudinal axis A is labeled with proximal and distal directions in FIGS. 1-3, wherein the proximal and distal directions are referenced with respect to a user such as a surgeon operating the tool 100. A hopper 110 with an internal volume for storing bone graft material, indicated schematically in FIG. 2, is connected to the hopper end 106 of the cannula 102 with the internal volume of the hopper 110 in communication with the inner lumen 104 of the cannula 102 for delivery of bone graft material from the hopper 110 out through the delivery tip 108 of the cannula 102.

An output shaft 112 within the inner lumen 104 extends along the longitudinal axis A. As shown in FIG. 3, output shaft 112 can be separated into a proximal section and a distal section, but those skilled in the art will readily appreciate that output shaft 112 can be made as a single unitary piece without departing from the scope of this disclosure. The output shaft 112 includes a helical screw thread 114 extending radially outward from the output shaft 112 toward an inner surface of the cannula 102. A pair of diametrically opposed paddles 116 extends radially outward from the output shaft 112 within the internal volume of the hopper 110 for agitating bone graft material within the hopper 110 upon rotation of the output shaft 112. The paddles 116 are proximal of the helical screw thread 114.

An actuator 118 is connected to the hopper 110 and to the output shaft 112 to drive the output shaft 112 rotationally relative to the hopper 110 and cannula 102. The actuator 118 includes a bottom cam 120 mounted stationary relative to the hopper 110. A driver 122 is engaged for sliding linear motion relative to the bottom cam 120 along the longitudinal axis A. A top cam 124 is mounted stationary relative to the hopper 110. The output shaft 112 includes a set of cam followers 126 configured to alternately cam with the bottom cam 120 and with the top cam 124 to convert reciprocating linear input movement of the driver 122 into motion of the output shaft 112 that alternates between linear motion extending distally along the longitudinal axis A to push bone graft material out of the inner lumen 104 of the cannula 102 and combined linear and rotary motion withdrawing in a proximal direction toward the internal volume of the hopper 110. As will be explained in further detail below, continued reciprocating linear input movement of the driver 122 repeatedly moves bone graft material from the hopper 110 to the delivery tip 108 of the cannula 102.

A biasing member 128 is mounted, e.g., with one end stationary within top cam 124, to bias the output shaft 112 in a distal direction toward the delivery tip 108 of the cannula 102. The biasing force of the biasing member 108 must be overcome to move the driver 122 and output shaft 112 in a proximal direction away from the delivery tip 108 of the cannula 102.

The top cam 124 includes a set of camming surfaces 130, identified in FIGS. 4-9, configured to rotate the output shaft 112 as the driver 122 presses the cam followers 126 of the drive shaft 112 into the respective camming surfaces 130 of the top cam 124. The bottom cam 120 includes a set of camming surfaces 132, identified in FIGS. 3 and 4-9, configured to rotate the output shaft 112, in the same direction as the camming surfaces 130 rotate the output shaft 112, as the output shaft 112 is biased toward the delivery tip 108 of the cannula 102 to rotationally position the output shaft 112 for a subsequent camming against the camming surfaces 130 of the top cam 124.

Figure 10:
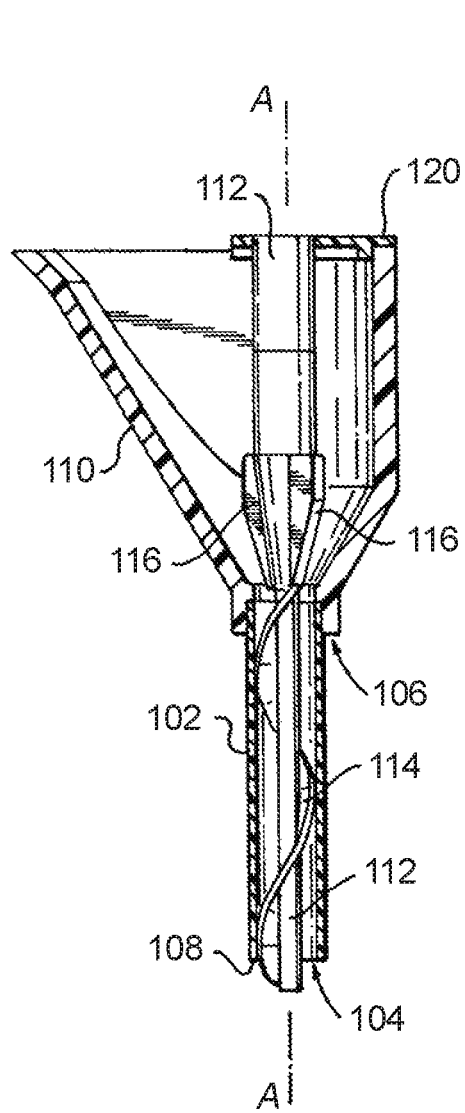
FIG. 10 is a partially cross-sectional side elevation view of a portion of the tool of FIG. 1, showing the output shaft position corresponding to the actuator position of FIG. 4.
Figure 11:
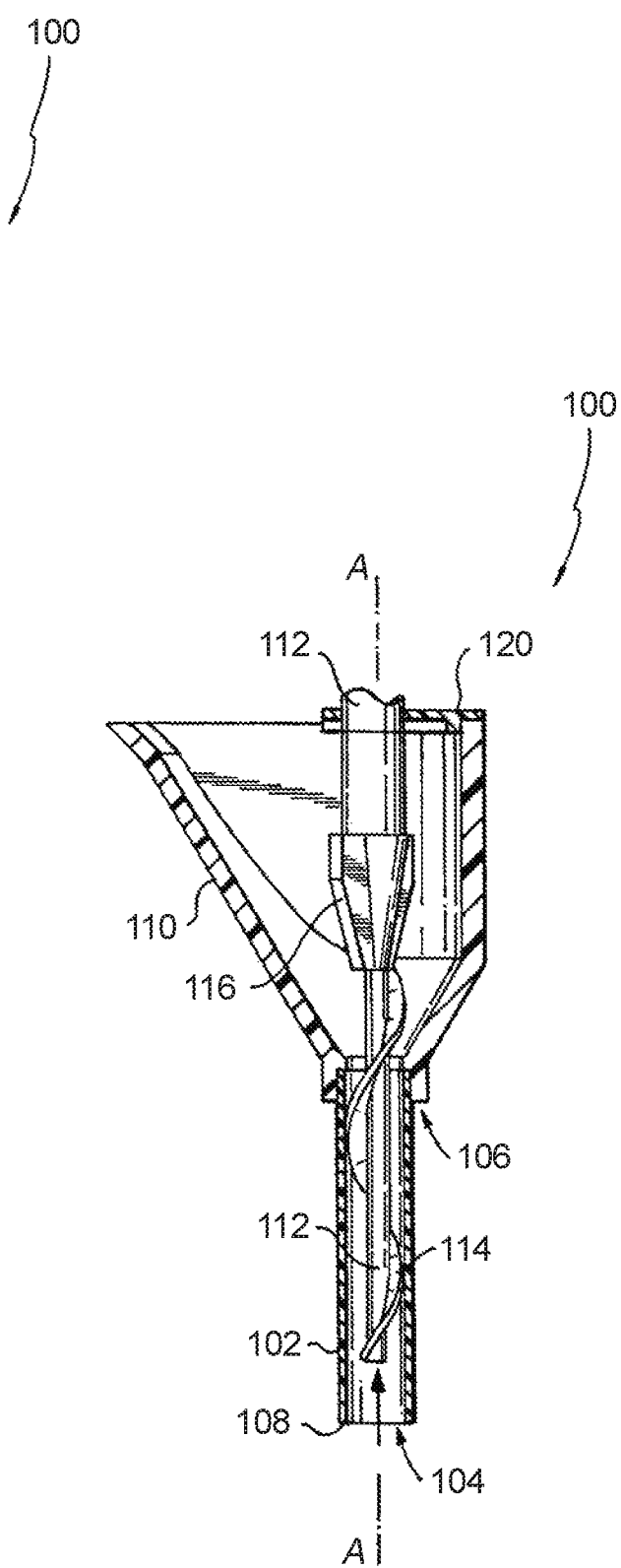
FIG. 11 is a partially cross-sectional side elevation view of a portion of the tool of FIG. 1, schematically showing the output shaft winding upward corresponding to the actuator positions in FIGS. 5-6.

With reference now to FIGS. 10-11, a method of delivering bone graft material to a bone graft site includes starting from the output shaft position shown in FIG. 10 and withdrawing a portion of the output shaft 112 into the hopper 110 housing bone graft material (bone graft material is not shown in FIG. 10, but see FIG. 2) as shown in FIG. 11 to engage the bone graft material in the hopper 110. Withdrawing the portion of the output shaft 112 into the hopper 110 includes withdrawing the helical screw thread 114 helically by combined linear and rotary motion relative to longitudinal axis A as indicated schematically in FIG. 11 by the large axial and circumferential arrows. This helical motion follows the helical screw thread 114 to keep in place bone graft material in a cannula 102 that houses at least a portion of the helical screw thread 114.

Figure 12:
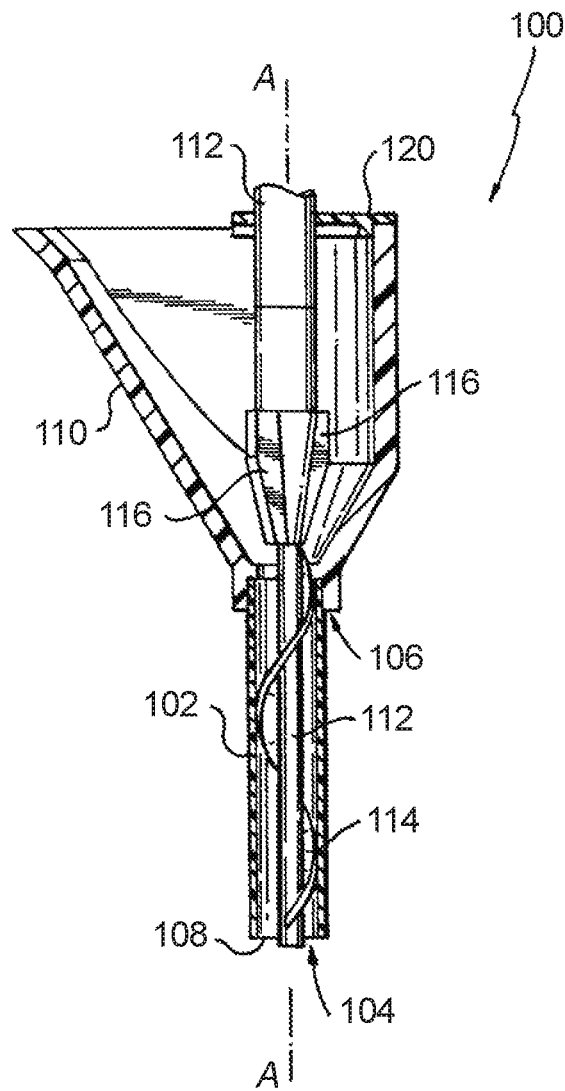
FIG. 12 is a partially cross-sectional side elevation view of a portion of the tool of FIG. 1, schematically showing the output shaft extending axially corresponding to the actuator position shown in FIG. 7.
Figure 13:
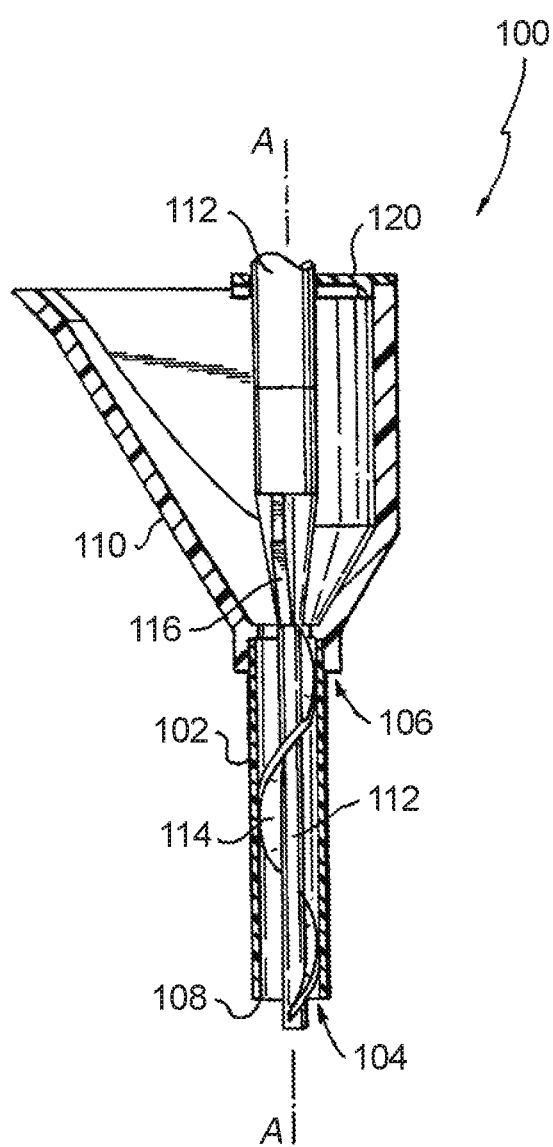
FIG. 13 is a partially cross-sectional side elevation view of a portion of the tool of FIG. 1, schematically showing a small helical indexing motion of the output shaft corresponding to the actuator positions shown in FIGS. 8 and 9.
Figure 14:
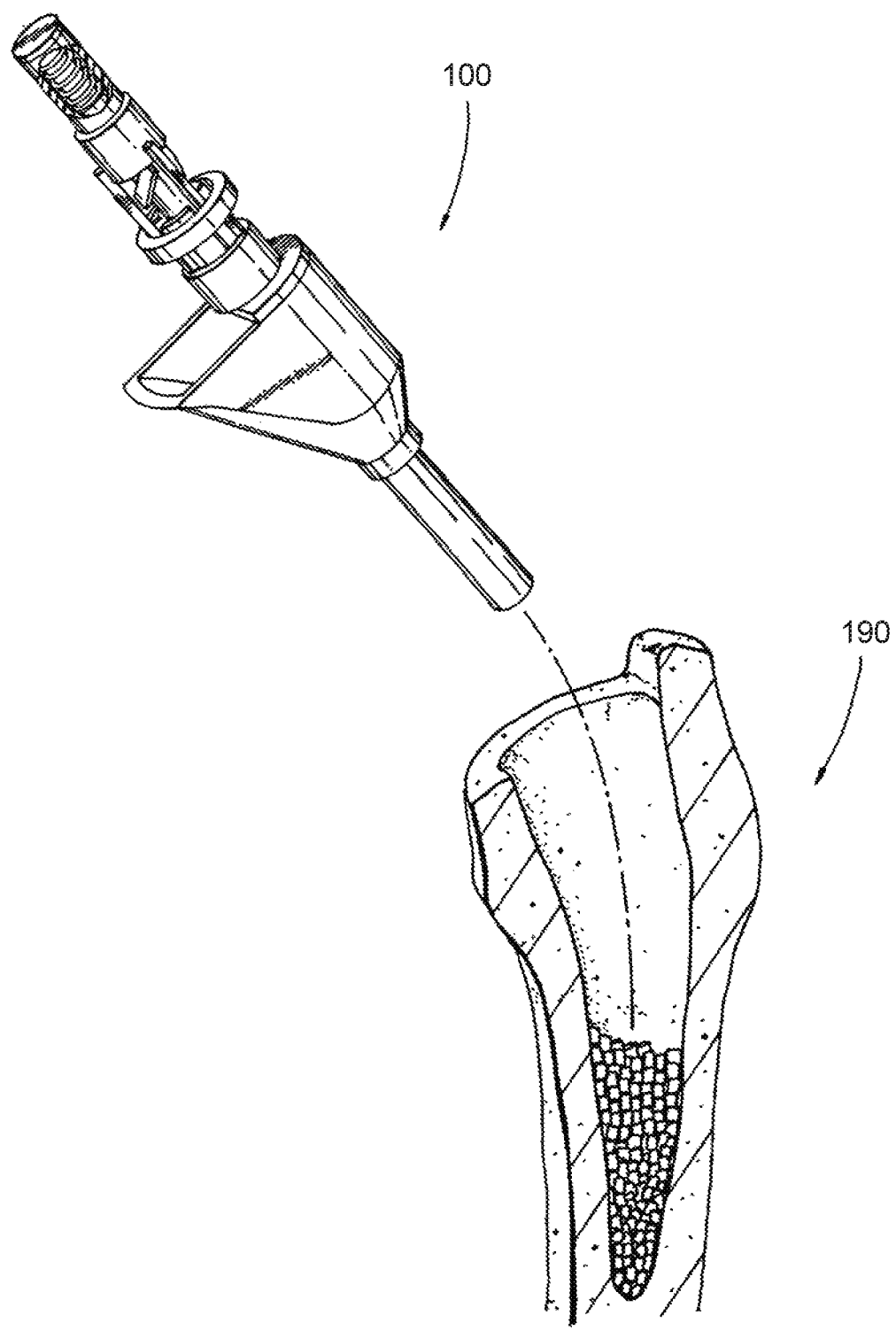
FIG. 14 is a schematic view of a method in accordance with the present invention, indicating delivery of bone graft material to a proximal hip during a hip revision procedure.
Figure 15:
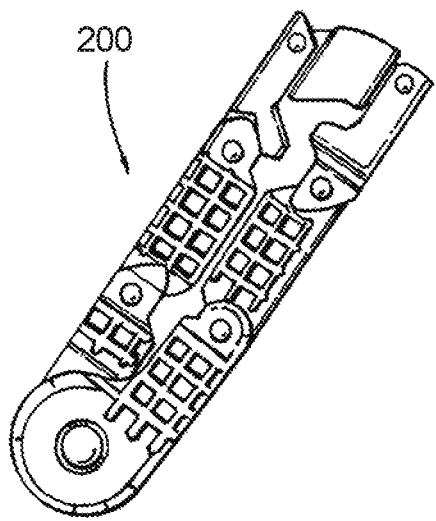
FIG. 15 is a schematic view of an interbody device in an unexpanded state.

Referring now to FIG. 12, the method also includes pushing the portion of the output shaft 112 axially out of the hopper 110 to deliver bone graft material from the hopper 110 to a bone graft site, pushing bone graft material engaged with the helical screw thread 114 out of the hopper 110 and out of the inner lumen 104 of the cannula 102. For at least part of this outward stroke, the actuator 118 is configured to extend the output shaft 112 axially along the longitudinal axis A in a direction out of the hopper 110 without rotating the output shaft 112. The large arrow in FIG. 12 schematically indicates this axial movement. As the large diagonal arrow in FIG. 13 indicates, the extension motion of the output shaft 112 and the helical screw thread 114 of FIG. 12 completes with a small helical indexing motion at the end of the outward stroke of the output shaft 112. This resets the cam followers 126 for a subsequent cycle of camming with the camming surfaces 130 of the top cam 124 (the cam followers 126 and camming surfaces 130 are shown in FIGS. 4-9). The method includes agitating the bone graft material within the hopper 110 using rotary motion of the paddles 116 extending radially from the output shaft 112 to facilitate loading bone graft material into the inner lumen 104 of the cannula 102. The rotary motion of the paddles 116 is demonstrated by comparing the positions of the paddles 116 in FIGS. 10-13.

Figure 17:
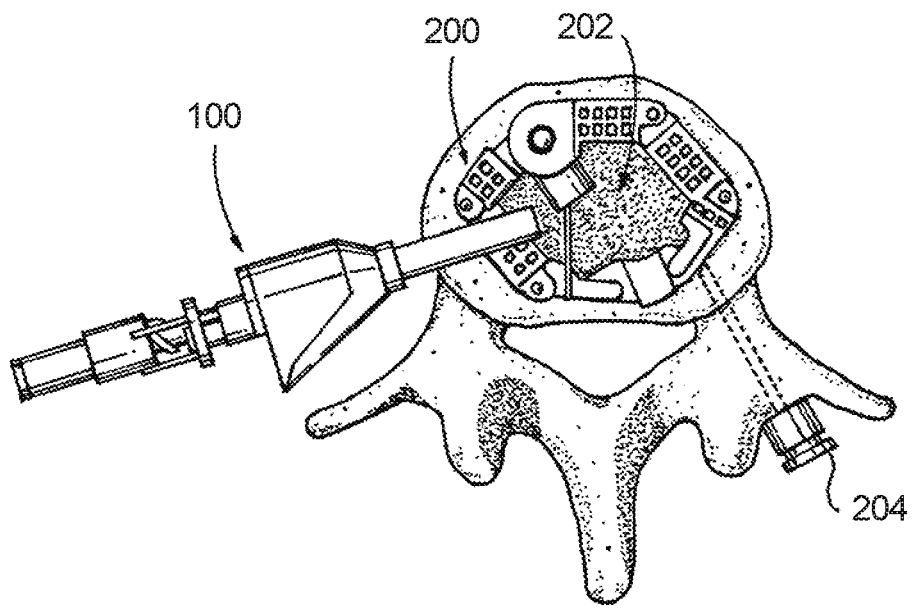
FIG. 17 is a schematic view of a method in accordance with the present invention, showing the interbody device of FIG. 16 with a tool of FIG. 1 delivering bone graft material to the inside of the interbody device.

The axial movement in FIG. 12 of the output shaft 112 and its helical screw thread 114 pushes or ejects bone graft material out of the inner lumen 104 at the delivery tip 108 of the cannula 102 and allows a surgeon to deliver and even compact bone graft material into a bone graft site, e.g. starting at the bottom of a hole in a bone, such as when using bone graft material in a hole in a spinal arch pedicle to improve bone screw fixation. For example, this can improve sacral or spinal pedicle screw fixation in osteoporotic applications. FIG. 17 shows a pedicle screw 204 for reference. Compacting bone graft material into the bone graft site is possible by applying pressure from at least one of the cannula 102, the helical screw thread 114, and/or the output shaft 112. Tool 100 enables a surgeon to deliver and compact bone graft material from the hopper 110 into at least two different bone graft sites with a single bone graft delivery tool 100 during a single surgical procedure.

With reference again to FIG. 4, the actuator 118 converts reciprocating linear input movement on the driver 122 in the axial direction along longitudinal axis A into motion of the output shaft 112 that alternates between the linear extending motion along the longitudinal axis A and the helical withdrawing motion described above so that continued reciprocating linear input movement of the driver 122 repeatedly moves bone graft material from the hopper 110 to the delivery tip 108 of the cannula 102. From the initial position shown in FIG. 4, which corresponds to the position of the output shaft 112 shown in FIG. 10, the driver 122 moves upward or proximal as indicated by the large arrow in FIG. 5. This upward motion in the axial direction pushes the output shaft 112 proximally, its cam followers 126 forced upward by the arms 134 of the driver 122, driving the cam followers 126 into rotational camming against the camming surfaces 130 of the top cam 124. This proximal axial motion ends in the position shown in FIG. 6, as indicated by the large arrow in FIG. 6. The actuator positions of FIGS. 5 and 6 correspond to the motion of output shaft 112 indicated in FIG. 11. The biasing force from the biasing member 128 (not shown in FIGS. 4-9, but see FIGS. 1-3) pushes the output shaft 112 downward as shown in FIG. 7, flexing the arms 134 of the driver radially outward so the cam followers 126 can pass downward past the arms 134. The actuator position of FIG. 7 corresponds to the position of the output shaft 112 shown in FIG. 12.

Figure 8:
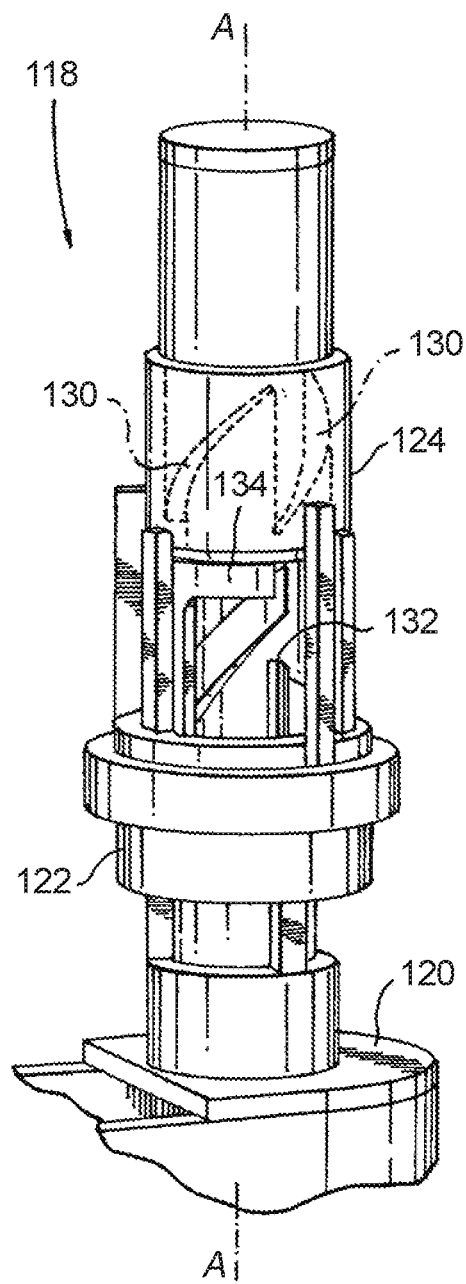
FIG. 8 is a schematic perspective view of the actuator of FIG. 4, showing the end of the downward movement of the output shaft.
Figure 9:
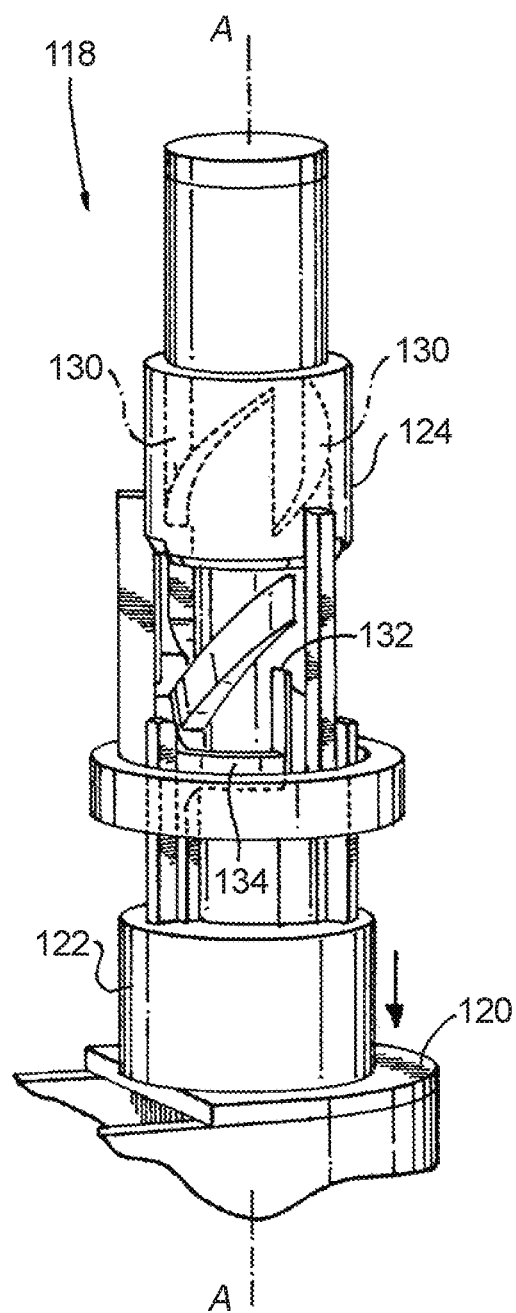
FIG. 9 is a schematic perspective view of the actuator of FIG. 4, showing the downward movement of the driver to return the actuator to the state of FIG. 4.

As shown in FIG. 8, the cam followers 126 bottom out on the respective camming surfaces 132 of the bottom cam 120.

As the biasing member 128 continues to drive the output shaft 112 downward, the camming surfaces 132 cause the small helical movement at the end of the downward stroke to reset the position of the cam followers 126 for the next upward movement, where the cam followers 126 come to rest against respective shelves 136 of the bottom cam 120. The shelves 136 are identified in FIG. 3. Finally, the driver 122 can be returned to its initial position as indicated schematically by the large arrow in FIG. 9. From here, the next reciprocating linear movement of the driver 122 can be initiated beginning again from the position shown in FIG. 4. The actuator positions of FIGS. 8 and 9 correspond to the motion of the output shaft indicated in FIG. 13. Impacting the bone graft material after it is delivered to the bone graft site can allow it to be impacted for better purchase of bone screws, densifying the bone where a bone screw is to be fixated.

Figure 16:
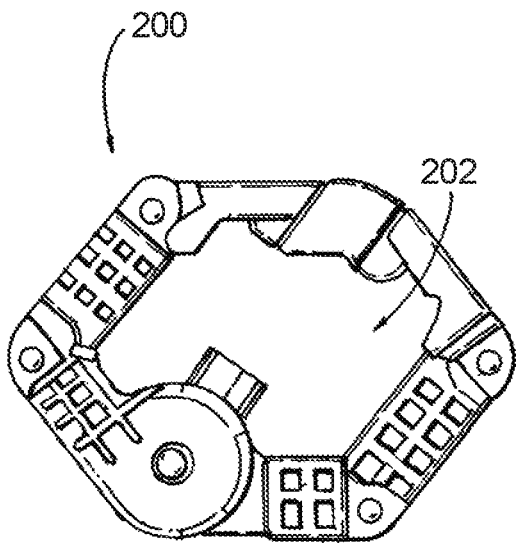
FIG. 16 is a schematic view of the interbody device of FIG. 15 in an expanded state.

Tools and methods as described herein facilitate tamping bone graft material in place in difficult to reach places, such as during minimally invasive surgery. For example, in lumbar interbody fusion (LIF), an intervertebral body 200 can be delivered to the intervertebral space in an unexpanded state, shown in FIG. 15, in a minimally invasive procedure. Once in place, the intervertebral body can be expanded as shown in FIG. 16, and tool 100 as disclosed herein can be used to deliver bone graft material to the interior space 202 of the expanded intervertebral body, as indicated in FIG. 17. Those skilled in the art will readily appreciate that this can be accomplished using an anterior approach (ALIF), or any other approach such as posterior (PLIF), transforaminal (TLIF) or extreme lateral (XLIF). While described with examples relating to spinal and sacral procedures, those skilled in the art will readily appreciate that tools and methods as described herein can readily be applied to any suitable orthopedic application without departing from the scope of this disclosure. For example, in revision hips, bone graft material can be impacted into the proximal femur 190 using tools and methods described herein to improve fixation, as indicated schematically in FIG. 14. Any suitable bone graft material can be used in conjunction with tools and methods as described herein including calcium sulfate, autograft, allograft, bone graft protein, or the like, without departing from the scope of this disclosure.

The methods and systems of the present disclosure, as described above and shown in the drawings, provide for delivery and compaction of bone graft material with superior properties including ease of use and the ability to deliver and compact bone graft material to multiple bone graft sites using a single tool in a given surgery. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A tool for delivery and/or compaction of bone graft material comprising:
    a cannula with an inner lumen extending along a longitudinal axis from a hopper end of the cannula to a delivery tip of the cannula;
    a hopper with an internal volume for storing bone graft material, wherein the hopper is connected to the hopper end of the cannula with the internal volume of the hopper in communication with the inner lumen of the cannula for delivery of bone graft material from the hopper to the delivery tip of the cannula;
    an output shaft within the inner lumen extending along the longitudinal axis, the output shaft including a helical screw thread extending radially outward from the output shaft toward an inner surface of the cannula; and
    an actuator connected to the hopper and to the output shaft to drive the output shaft rotationally relative to the hopper and to the cannula,
    wherein the actuator is configured to drive motion of the output shaft that alternates between a first stroke motion including linear motion extending along the longitudinal axis to push bone graft material out of the inner lumen of the cannula and a second stroke motion including combined linear and rotary motion withdrawing in a direction toward the internal volume of the hopper so that continued alternating between the first stroke motion and the second stroke motion repeatedly moves bone graft material from the hopper to the delivery tip of the cannula, wherein in the first stroke motion the actuator is configured to extend the output shaft axially along the longitudinal axis in a direction out of the hopper for pushing bone graft material engaged with the helical screw thread out of the hopper and out of the inner lumen of the cannula, wherein for at least part of the first stroke motion, the actuator is configured to extend the output shaft axially along the longitudinal axis in a direction out of the hopper without rotating the output shaft.

2. The tool as recited in claim 1, wherein in the second stroke motion the actuator is configured to withdraw the output shaft axially along the longitudinal axis in a direction into the hopper while rotating the output shaft for engaging bone graft material with the helical screw thread in the hopper.

3. The tool as recited in claim 1, wherein the actuator is configured to convert reciprocating linear input movement into motion of the output shaft that alternates between the first and second stroke motions so that continued reciprocating linear input movement repeatedly moves bone graft material from the hopper to the delivery tip of the cannula.

4. The tool as recited in claim 1, further comprising a paddle extending radially outward from the output shaft within the internal volume of the hopper for agitating bone graft material within the hopper upon rotation of the output shaft.

5. The tool as recited in claim 4, wherein the paddle is proximal of the helical screw thread.

6. The tool as recited in claim 1, wherein the actuator includes:
    a bottom cam mounted stationary relative to the hopper;
    a driver engaged for sliding linear motion relative to the bottom cam; and
    a top cam mounted stationary relative to the hopper,
    wherein the output shaft includes at least one cam follower configured to alternately cam with the bottom cam and with the top cam to convert reciprocating linear input movement of the driver into motion of the output shaft that alternates between linear motion extending along the longitudinal axis to push bone graft material out of the inner lumen of the cannula and combined linear and rotary motion withdrawing in a direction toward the internal volume of the hopper so that continued reciprocating linear input movement of the driver repeatedly moves bone graft material from the hopper to the delivery tip of the cannula.

7. The tool as recited in claim 6, further comprising a biasing member mounted to bias the output shaft in a direction toward the delivery tip of the cannula, wherein biasing force of the biasing member must be overcome to move the driver and output shaft in a direction away from the delivery tip of the cannula.

8. The tool as recited in claim 6, wherein the top cam includes at least one camming surface configured to rotate the output shaft as the driver presses the at least one cam follower of the output shaft into the at least one camming surface of the top cam.

9. The tool as recited in claim 6, wherein the bottom cam includes at least one camming surface configured to rotate the output shaft as the output shaft is biased toward the delivery tip of the cannula to rotationally position the output shaft for a subsequent camming against the top cam.

10. A tool for delivery and/or compaction of bone graft material comprising:
   a cannula with an inner lumen extending along a longitudinal axis from a hopper end of the cannula to a delivery tip of the cannula;
   a hopper with an internal volume for storing bone graft material, wherein the hopper is connected to the hopper end of the cannula with the internal volume of the hopper in communication with the inner lumen of the cannula for delivery of bone graft material from the hopper to the delivery tip of the cannula;
   an output shaft within the inner lumen extending along the longitudinal axis, the output shaft including a helical screw thread extending radially outward from the output shaft toward an inner surface of the cannula; and
   an actuator connected to the hopper and to the output shaft to drive the output shaft rotationally relative to the hopper and to the cannula,
wherein the actuator is configured to drive motion of the output shaft that alternates between a first stroke motion including linear motion extending along the longitudinal axis to push bone graft material out of the inner lumen of the cannula and a second stroke motion including combined linear and rotary motion withdrawing in a direction toward the internal volume of the hopper so that continued alternating between the first stroke motion and the second stroke motion repeatedly moves bone graft material from the hopper to the delivery tip of the cannula, wherein the actuator is configured to convert reciprocating linear input movement into motion of the output shaft that alternates between the first and second stroke motions so that continued reciprocating linear input movement repeatedly moves bone graft material from the hopper to the delivery tip of the cannula.

11. A tool for delivery and/or compaction of bone graft material comprising:
   a cannula with an inner lumen extending along a longitudinal axis from a hopper end of the cannula to a delivery tip of the cannula;
   a hopper with an internal volume for storing bone graft material, wherein the hopper is connected to the hopper end of the cannula with the internal volume of the hopper in communication with the inner lumen of the cannula for delivery of bone graft material from the hopper to the delivery tip of the cannula;
   an output shaft within the inner lumen extending along the longitudinal axis, the output shaft including a helical screw thread extending radially outward from the output shaft toward an inner surface of the cannula; and
   an actuator connected to the hopper and to the output shaft to drive the output shaft rotationally relative to the hopper and to the cannula, wherein the actuator is configured to drive motion of the output shaft that alternates between a first stroke motion including linear motion extending along the longitudinal axis to push bone graft material out of the inner lumen of the cannula and a second stroke motion including combined linear and rotary motion withdrawing in a direction toward the internal volume of the hopper so that continued alternating between the first stroke motion and the second stroke motion repeatedly moves bone graft material from the hopper to the delivery tip of the cannula, wherein the actuator includes:
   a bottom cam mounted stationary relative to the hopper;
   a driver engaged for sliding linear motion relative to the bottom cam; and
   a top cam mounted stationary relative to the hopper,
   wherein the output shaft includes at least one cam follower configured to alternately cam with the bottom cam and with the top cam to convert reciprocating linear input movement of the driver into motion of the output shaft that alternates between linear motion extending along the longitudinal axis to push bone graft material out of the inner lumen of the cannula and combined linear and rotary motion withdrawing in a direction toward the internal volume of the hopper so that continued reciprocating linear input movement of the driver repeatedly moves bone graft material from the hopper to the delivery tip of the cannula.

12. The tool as recited in claim 11, further comprising a biasing member mounted to bias the output shaft in a direction toward the delivery tip of the cannula, wherein biasing force of the biasing member must be overcome to move the driver and output shaft in a direction away from the delivery tip of the cannula.

13. The tool as recited in claim 11, wherein the top cam includes at least one camming surface configured to rotate the output shaft as the driver presses the at least one cam follower of the output shaft into the at least one camming surface of the top cam.

14. The tool as recited in claim 11, wherein the bottom cam includes at least one camming surface configured to rotate the output shaft as the output shaft is biased toward the delivery tip of the cannula to rotationally position the output shaft for a subsequent camming against the top cam.

* * * * *